US008877810B2

(12) United States Patent
Konygin et al.

(10) Patent No.: US 8,877,810 B2
(45) Date of Patent: Nov. 4, 2014

(54) METHOD FOR PRODUCING MECHANICALLY ACTIVATED AMORPHOUS AND AMORPHOCRYSTALLINE COMPOUNDS OF GLUCONIC ACID CALCIUM SALT

(75) Inventors: Grigoriy Nikolaevich Konygin, Izhevsk (RU); Nikolaj Sergeevich Strelkov, Izhevsk (RU); Dmitriy Stanislavovich Rybin, Izhevsk (RU); Viktor Vladimirovich Pozdeev, Izhevsk (RU); Evgeny Petrovich Yelsukov, Izhevsk (RU); Dilara Rashiovna Sharafutdinova, Kazan (RU); Yuri Yakovlevich Efremov, Kazan (RU); Vladimir Yurievich Petukhov, Kazan (RU); Gabdrauf Gabdrashitovich Gumarov, Kazan (RU)

(73) Assignees: Grigoriy Nikolaevich Konygin, Izhevsk (RU); Dmitriy Stanislavovich Rybin, Izhevsk (RU); Nikolaj Sergeevich Strelkov, Izhevsk (RU)

( * ) Notice: Subject to any disclaimer, the term of this patent is extended or adjusted under 35 U.S.C. 154(b) by 377 days.

(21) Appl. No.: 12/669,907

(22) PCT Filed: Jun. 30, 2008

(86) PCT No.: PCT/RU2008/000403
§ 371 (c)(1),
(2), (4) Date: Mar. 30, 2011

(87) PCT Pub. No.: WO2009/014471
PCT Pub. Date: Jan. 29, 2009

(65) Prior Publication Data
US 2011/0178175 A1   Jul. 21, 2011

(51) Int. Cl.
*A61K 31/19*    (2006.01)
*C07C 59/105*    (2006.01)

(52) U.S. Cl.
CPC ........... *C07C 59/105* (2013.01); *C07B 2200/13* (2013.01)
USPC ........................................ 514/557

(58) Field of Classification Search
USPC ........................................ 514/557
See application file for complete search history.

(56) References Cited

FOREIGN PATENT DOCUMENTS

| RU | 94022264 | 4/1994 |
|---|---|---|
| RU | 2 268 053 | 5/2004 |

OTHER PUBLICATIONS

Konygin, G. N., et al. "Mechanoactivated Medical Preparation Calcium Gluconate: X-Ray Structural, Microscopic and X-Ray Electron Investigations.", 2005, Chemistry for Sustainable Development, vol. 13, 249-252.*
Kolygin G. N. et al. Mekhanoaktivirovanny lekarstvenny preparat kaltsya glukonat rentgenostrukturnye, mikroskopicheskie i rentgenoelektronnye issledovanya. Khimiya V interesakh X' ustoichivogo rasvitiya, 13, 2005, CTp. 249-252 Ctp. 250, left column, lines 1-42, drawings 1-3, p. 249, left column, line 10—right 1-17,20-36 A column, line 15.
Kolygin G. N. Nashi kosti budut krepche. ra3eTa "Nauka Urala" No X 1 (888), Jan. 2005, [on-line] [found on Nov. 21, 2008]. Found on the Internet:<URL:http://www.uran. ru/gazetanu/2005/01/nu01 Iwvmnu_p6_01_0 12005.h tm, p. 3, 2nd paragraph—p. 4 last paragraph.
Kaltsya glukonat. 2006, [on-line] [Found on Nov. 21, 2008]. Found on the InterneT:<URL:http://www.romat.kz/calcyi.html.
N.V. Toroptseva, et al. Osteoporosis: Possibilities of Prophylaxis with Calcium Preparations and Vitamin D, farmateka No. 5 (140), 2007, pp. 56-61.
N.V. Toroptseva, et al. New Bonviva Bisphosphonate for Treatment of Postmenopausal Osteoporosis, Osteoporosis and osteopathy, 2006, No. 2, pp. 32-45.

* cited by examiner

*Primary Examiner* — Ali Soroush
(74) *Attorney, Agent, or Firm* — Ladas & Parry LLP

(57) ABSTRACT

The invention relates to the mechanically activated amorphous and amorphocrystalline compounds and compositions based thereon. Crystalline gluconic acid calcium salt or its compound with excipients is treated in grinding activator devices either up to the input specific energy value of not greater than 10.4 kJ/g and achieving an amorphocrystalline state or up to the input specific energy value of no less than 10.5 kJ/g and achieving an amorphous state. The obtainable agents are assessed by means of X-ray diffraction, IR, NMR, EPR spectroscopy, mass- or chromato-mass-spectrometry, and a differential thermal analysis. The mechanically activated amorphous and amorphocrystalline compounds are used as an active principle for preparing pharmaceutical preparations. The invention can be used in medical and food industries in the production of biologically active agents, therapeutic-prophylactic means, medicinals and in practical medicine in treatment of acute osseous, dental and other diseases related to disorders of calcium metabolism in the organism.

8 Claims, 8 Drawing Sheets

Figure 1:
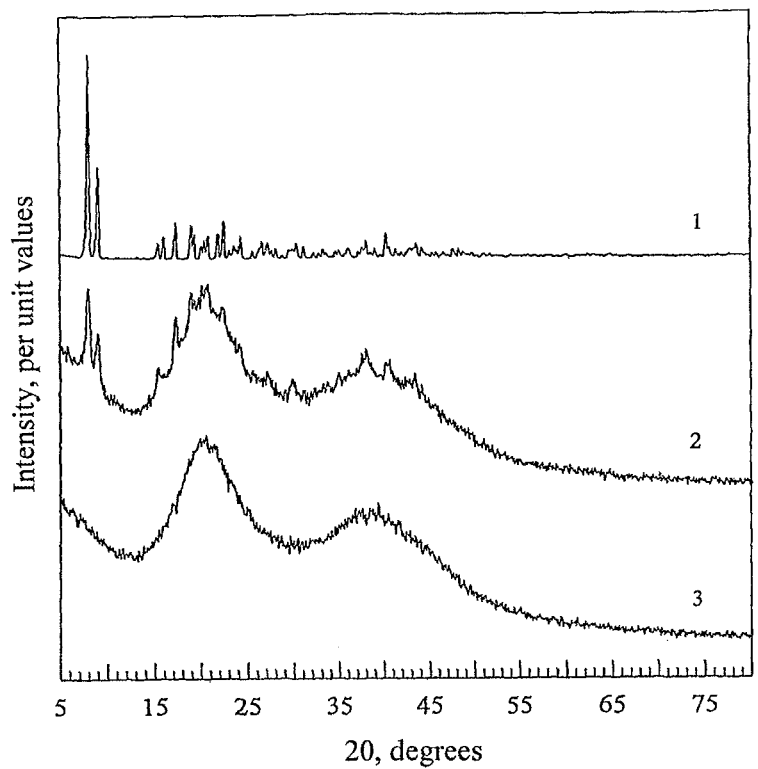

METHOD FOR PRODUCING MECHANICALLY ACTIVATED AMORPHOUS AND AMORPHOCRYSTALLINE COMPOUNDS OF GLUCONIC ACID CALCIUM SALT

The invention relates to a method for producing from a gluconic acid crystalline calcium salt having a pharmaceutical trade name "calcium gluconate", mechanically activated amorphous and amorphocrystalline forms of the gluconic acid calcium salt, mixtures based thereon, and pharmaceutical compositions.

They can be used in the medical industry for producing biologically active agents, therapeutic—prophylactic agents and drugs, for treatment of acute osseous, dental and other diseases caused by metabolic calcium disorders in an organism and also as additives to therapeutic-prophylactic agents and hygienic means.

The invention can be used in various branches of food industry and in agriculture, particularly in animal husbandry and veterinary science.

Methods for producing therapeutically effective and stable compositions with amorphous calcium gluconate forms are not described in literature.

A solid crystal matter with the chemical name of a gluconic acid calcium salt with the pharmaceutical trade name of calcium gluconate is known as the agent of a pharmacological group comprising macro- and microelements.

Calcium gluconate relates to the pharmacological group of agents which together with vitamins and other bioactive agents are compulsory elements enabling a normal course of vital processes to proceed in human beings. Calcium plays a manysided role in the active life of an organism: participates in nervous impulses transmission, maintenance of the tone of skeleton and smooth muscles, myocardial functioning, blood coagulation processes and other physiological processes and in forming and preserving an integrity of bone tissues. Various pathological processes, specifically tetany, the malfunction of the skeleton and smooth muscles, cardio-vascular system, blood coagulation disorders, osteoporosis, many acute dental diseases are manifestation of a calcium deficit in the organism. In this connection, the calcium gluconate finds a wide variety of application in medicine.

However, the conventional calcium gluconate and therapeutic compositions containing a calcium gluconate active ingredient, just like all other currently known calcium preparations, demonstrate insufficient therapeutic efficiency for the effective conservative treatment of diseases attributable to metabolic calcium disorders in an organism, particularly osteoporosis and other acute osseous and dental diseases and more than that the osteoporosis also in virtue of a low efficacy of calcium preparations available in an arsenal of medicine, in particular, is recognized today global and directly life connected public health problem. The task of developing the therapeutically more effective forms of calcium preparations and methods for producing same is of current interest and of global social and economic importance.

Known are amorphous calcium compounds (amorphous phosphate, phosphate fluoride, carbonate phosphate, calcium carbonate phosphate fluoride) being obtained chemically and a method of tooth treatment using amorphous compounds by way of application to tooth tissue or inside /1/. The method is disadvantageous in that the application of amorphous calcium compounds to the tooth tissue does not solve the problem of normalization of calcium metabolism of an organism in general and is directed only at treating tooth defects but not at removing causes thereof Known is a method of treatment of hypocalciumenia, osteoporosis, fractures /2/ using amorphous-rendered mechanically activated calcium preparations. However, the claimed fields of use of the invention do not embrace the entire spectrum of diseases, dental ones included, and, therefore, the method does not solve, either, all problems connected with disorders of calcium metabolism in an organism.

The task of the present invention is to produce mechanically activated amorphous and amorphocrystalline compounds and compositions of a gluconic acid calcium salt, creation of pharmaceutical therapeutically effective preparations based thereon to provide a normal course of active life processes in a human body and treatment of a wide range of diseases attributable to metabolic calcium disorders in the organism, particularly acute parodontal diseases, widening of an arsenal of pharmaceutical preparations and creation of bioactive additives in food products, therapeutic-prophylactic and hygienic means.

A technical result is attained in the claimed invention by producing a mechanically activated amorphous gluconic acid calcium salt while treating a crystalline gluconic acid calcium salt in energy—strength grinding activator devices during certain times necessary for a specific energy of no less than 10.5 kJ/g to be supplied.

Besides, the technical result is attained in the claimed invention also by way of obtaining the compound of a mechanically activated amorphous gluconic acid calcium salt with pharmaceutically acceptable excipients in a ratio of ingredients, wt.%, as follows:

| | |
|---|---|
| Mechanically activated amorphous gluconic acid calcium salt | 94-97 |
| talc | 2-1 |
| starch | 2-1 |
| calcium stearate | 2-1 |

Besides, the technical result in the claimed invention is attained also by way of mixing a gluconic acid calcium salt with pharmaceutically acceptable excipients in a ratio of ingredients, wt. %, as follows:

| | |
|---|---|
| Gluconic acid crystalline calcium salt | 94-97 |
| talc | 2-1 |
| starch | 2-1 |
| calcium stearate | 2-1 | and by sequentially treating same in energy-strength grinding activator devices during certain times necessary for a specific energy of no less than 10.5 kJ/g to be supplied.

Production of a mechanically activated amorphous gluconic acid calcium salt and the mechanically activated amorphous composition of a gluconic acid calcium salt is assessed by:

homogeneous diffuse halo in an X-ray powder diffraction spectrum;

shift of the centre of gravity lines of an absorption region of 3000-3600 $cm^{-1}$ to a region of great wave numbers thru the value of not greater than 200 $cm^{-1}$, presence of absorption bands with frequencies of 3308±20, 2933±10, 1602±10, 1420±10 with an arm of 1260±40, 1085±10, 1044±10, 877±10, 682±10, 577±10 $cm^{-1}$ and an additional absorption band having a frequency of 947±10 $cm^{-1}$ in an IR spectrum (KBr);

reducing endotherm peaks in the temperature range of 125 to 165° C. and increasing a peak in the temperature range of 30 to 100° C. in a differential thermal assay (DTA);

presence of an intensive single electronic paramagnetic resonance line (EPR) with a g-factor of 2.000 to 2.006 and a width of 8 to 9 E;

occurrence of a fine structure unresolved wide line in the regions of 60-90 ppm and 170-190 ppm in $^{13}$C nuclear magnetic resonance spectra (NMR);

shift of the resonant lines of aqueous solutions thereof in a region of 62.8-179.2 ppm thru the value of not greater than 0.1 ppm in $^{13}$C NMR-spectra;

shift of the resonant lines of aqueous solutions thereof in the regions of 1.2-4.95 ppm thru the value of not greater than 0.02 ppm in $^1$H NMR-spectra;

increasing the 160 m/z line intensities of mechanically activated samples no less than 2.5 times and 780-1000 m/z lines of solution extracts thereof in ethanol not less than 3 times in a mass-spectroscopic analysis.

The technical result in the claimed invention is attained also by way of producing a mechanically activated amorphocrystalline gluconic acid calcium salt in treatment of the gluconic acid calcium salt in energy-strengh grinding activator devices during certain times necessary for a specific energy of no less than 10.4 kJ/g to be supplied.

Besides, the technical result in the claimed invention is attained also by way of producing a compound of a mechanically activated amorpho-crystalline gluconic acid calcium salt with pharmaceutically acceptable excipients in a ratio of ingredients, wt. %, as follows:

| | |
|---|---|
| amorpho-crystalline gluconic acid calcium salt | 94-97 |
| talc | 2-1 |
| starch | 2-1 |
| calcium stearate | 2-1 |

Besides, the technical result in the claimed invention is attained also by way of blending a gluconic acid calcium salt with pharmaceutically acceptable excipients in a ratio of ingredients, wt. %, as follows:

| | |
|---|---|
| crystalline gluconic acid calcium salt | 94-97 |
| talc | 2-1 |
| starch | 2-1 |
| calcium stearate | 2-1 | and by sequentially treating in energy-strengh grinding activator devices during certain times necessary for a specific energy of no less than 10.4 kJ/g to be supplied.

Production of a gluconic acid mechanically activated amorpho-crystalline gluconic acid calcium salt and a mechanically activated amorphocrystalline gluconic acid composition is assessed by:

simultaneous presence of a diffuse halo and structural crystal reflexes in an X-ray powder diffraction spectrum;

shift of the centre of gravity of an absorption region of 3000-3600 cm$^{-1}$ to the region of great wave numbers thru the value of not greater than 200 cm$^{-1}$, presence of an absorption band with frequencies 3480±10, 3241±30, 2933±10, 2912±10, 1597±10, 1392±20, 1306±10, 1296±10, 1085±10, 1044±10, 973±10, 908±10, 881±10, 699±10, 565±10 cm$^{-1}$ and an additional absorption band with a frequency of 947±10 cm$^{-1}$ in an IR spectrum;

occurrence of fine structure low-resolution wide lines in the regions of 60-90 ppm and 170-190 ppm in $^{13}$C NMR spectra;

shift of the resonant lines of their aqueous solutions in a region of 62.8-179.2 ppm thru the value not greater than 0.09 ppm in $^{13}$C NMR spectra;

shift of the resonant lines of their aqueous solutions in a region of 1.2-4.95 ppm thru the value of not greater than 0.015 ppm in $^1$NMR spectra:

increasing 160 m/z line intensities of mechanically activated samples not more than 2.5 times and 780-1000 m/z lines of solution extracts thereof in ethanol not more than 3 times in a mass-spectroscopic analysis;

presence of an intensive single EPR line with g-factor of 2.000 to 2.006 and a width of 8 to 9 E.

On the basis of amorphous compounds and compositions there are produced pharmaceutical preparations for treatment of wide variety of diseases necessitated by calcium deficiency in an organism in the form of a powder, tablet, capsule, solution, gel, to mention only few, which are used perorally 1-6 times a day, 0.2-6 g doses, a course of no less than 1 month.

FIGS. 1-10 show the results of research carried out by various methods into initial, mechanically activated amorphous and amorphocrystalline compositions calcium gluconate.

FIG. 1: X-ray powder diffraction diagrams (Cu K$_\alpha$radiation) of the following samples:

initial gluconic acid crystalline calcium salt, curve 1:

mechanically activated gluconic acid amorphocrystalline calcium salt, curve 2;

mechanically activated gluconic acid amorphous calcium salt, curve 3.

X-ray powder diffraction patterns were registered on an X-ray diffraction pattern DRON-3M apparatus in a monochromatic Cu K$_\alpha$-radiation.

A diffraction pattern of calcium gluconate treated in a grinding activator device with the input specific energy of 10.8 kJ/g (curve 3) is devoid of crystal reflexes and represents a diffuse halo characteristic of an amorphous substance. In the powder diffraction pattern of an amorphocrystalline gluconic acid calcium salt treatable in the grinding activator device with the input specific energy of 3.6 kJ/g (curve 2) concurrently present are amorphous diffuse halo and structural crystal reflexes corresponding to the content of an amorphous phase≈90 and a crystal phase 10 wt. %, respectively. Unlike those as mentioned above, the diffraction pattern of the known crystal compound of a gluconic acid calcium salt (curve 1) contains a kit of structural reflexes characteristic of a crystalline state.

Figure 2:
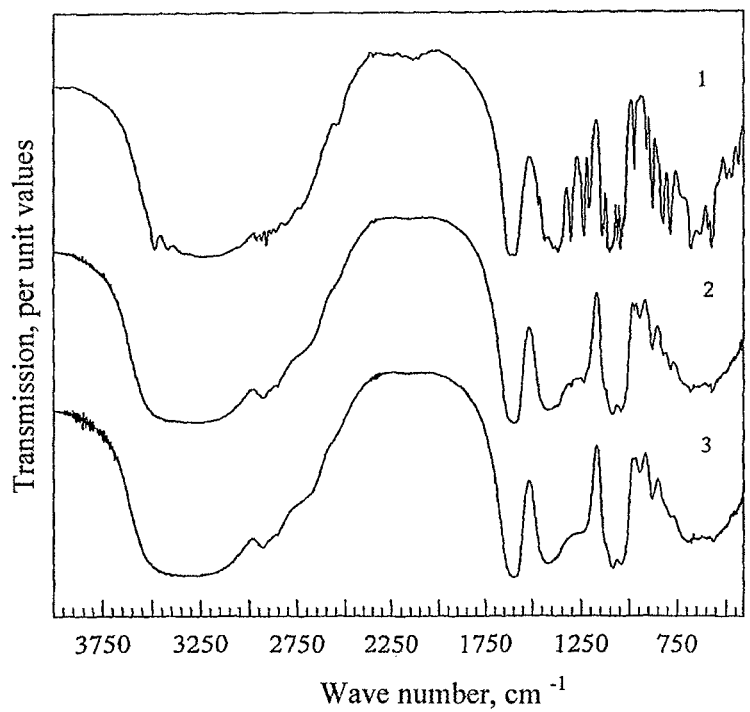

FIG. 2: IR-spectra of the following samples:

initial gluconic acid crystalline calcium salt, curve 1;

mechanically activated amorphocrystalline gluconic acid calcium salt, curve 2;

mechanically activated amorphous gluconic acid calcium salt, curve 3.

IR transmission spectra were plotted on an IR Fourier spectrometer FSM-1202. Samples were mixed with KBr (IR—degree of purity) and tabletted. All spectra were registered, 64 scans (the repeated measurements of each and every result), 1 cm$^{-1}$ resolution.

In the IR-Fourier spectrum of the mechanically activated amorphocrystalline gluconic acid calcium salt composition (curve 2), absorption bands have a less resolved line structure as distinct from the well resolved spectrum of a gluconic acid calcium salt in a crystalline state (curve I). The centre of gravity of an absorption region of 3000-3600 cm$^{-1}$ is displaced to an area of great wave numbers thru the value of not greater 200 cm$^{-1}$. The absorption bands with frequencies of 3480±10, 3241±30, 2933±10, 2912±10, 1597±10, 1392±20, 1306±10, 1296±10, 1085±10, 1044±10, 973±10, 908±10, 881±10, 699±10, 565±10 cm$^{-1}$ are observed as is an additional absorption band with the frequency of 947±10 cm$^{-1}$.

In the IR-Fourier spectrum of a mechanically activated amorphous form (curve 3) there are low-resolved line structure, the centre-of-gravity shift of an absorption region of 3000-3600 cm$^{-1}$ to an area of great wave numbers thru the value of not greater than 200 cm$^{-1}$, absorption bands with frequencies of 3308±20, 2933±10, 1602±10, 1420±10, with an arm of 1260±40, 1085±10, 1044±10, 877±10, 682±10, 577±10 cm$^{-1}$ and there is observed an additional absorption band with the frequency of 947±10 cm$^{-1}$.

The above-cited data show a change in the oscillation spectrum of mechanically activated samples partially preserving a calcium cation chemical bond with a gluconic acid anion, reduction of the number of hydrogen bonds (shift of the centre of gravity of a wide OH-group 3000-3600 cm$^{-1}$ absorption band to an area of great wave numbers) and formation of complexes and gluconic acid salt compositions with cyclic saccharides.

Figure 3:
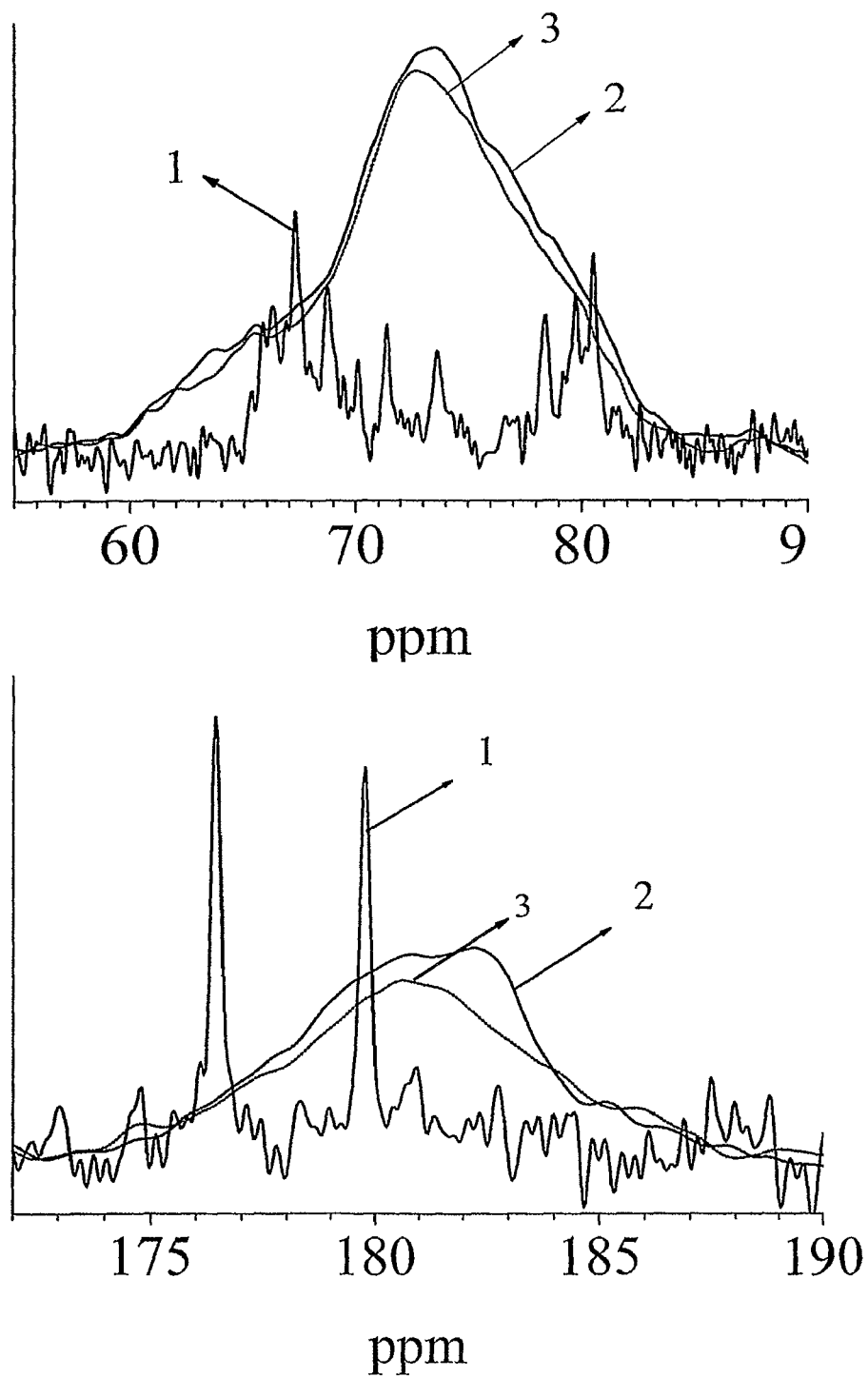

FIG. 3: $^{13}$C NMR spectra of solid state samples:
initial crystalline gluconic acid calcium salt, curve 1:
mechanically activated amorphocrystalline gluconic acid calcium salt, curve 2;
mechanically activated amorphous gluconic acid calcium salt, curve 3.

NMR-spectra were plotted on a pulse NMR spectrometer with Fourier transformation AVANCE-400 Bruker at the temperature of 295 K.

In amorphous form (curve 3) and amorphocrystalline salt (curve 2) $^{13}$C NMR spectra in an area of 60-90 ppm and 170-190 ppm are observed the wide lines of a fine unresolved structure. In $^{13}$C NMR spectra of a crystalline gluconic acid calcium salt in the same areas there is observed a well resolved fine structure of resonance absorption NMR spectra (curve 1).

It can really be seen from data cited that while machining a gluconic acid calcium salt crystal compound in energy-strength grinding activator devices there occurs a change in a local calcium gluconate molecular structure characterized by an increase in the number of unequivalent local atomic states of carbon atoms characteristic of a disordered crystalline or amorphous state of matter.

Figure 4:
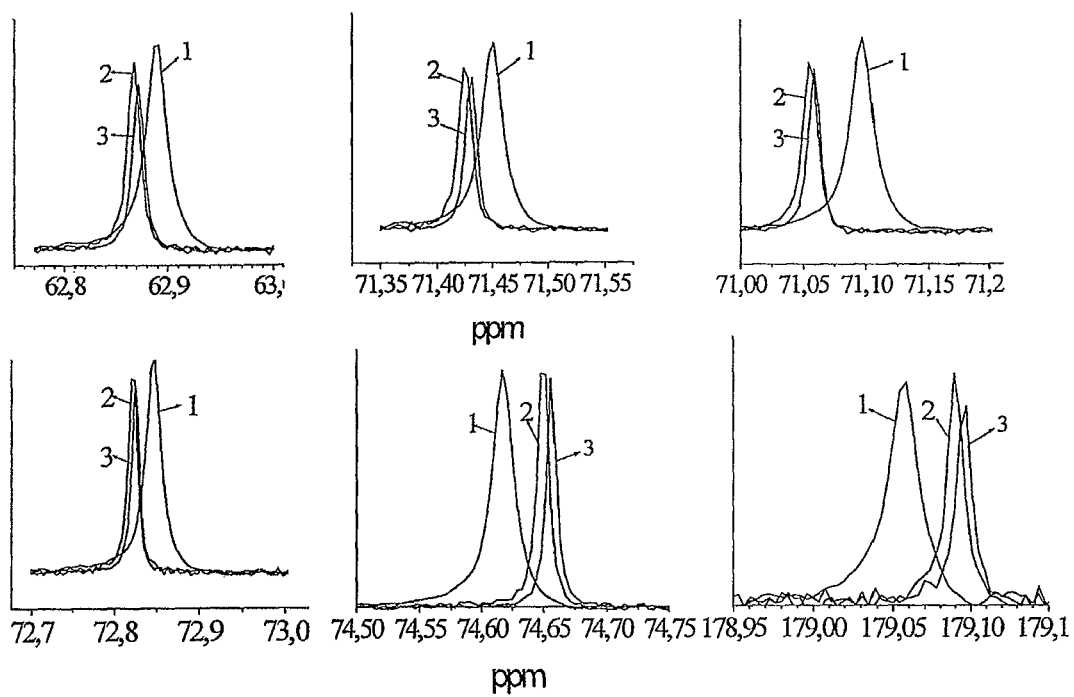
Figure 5:
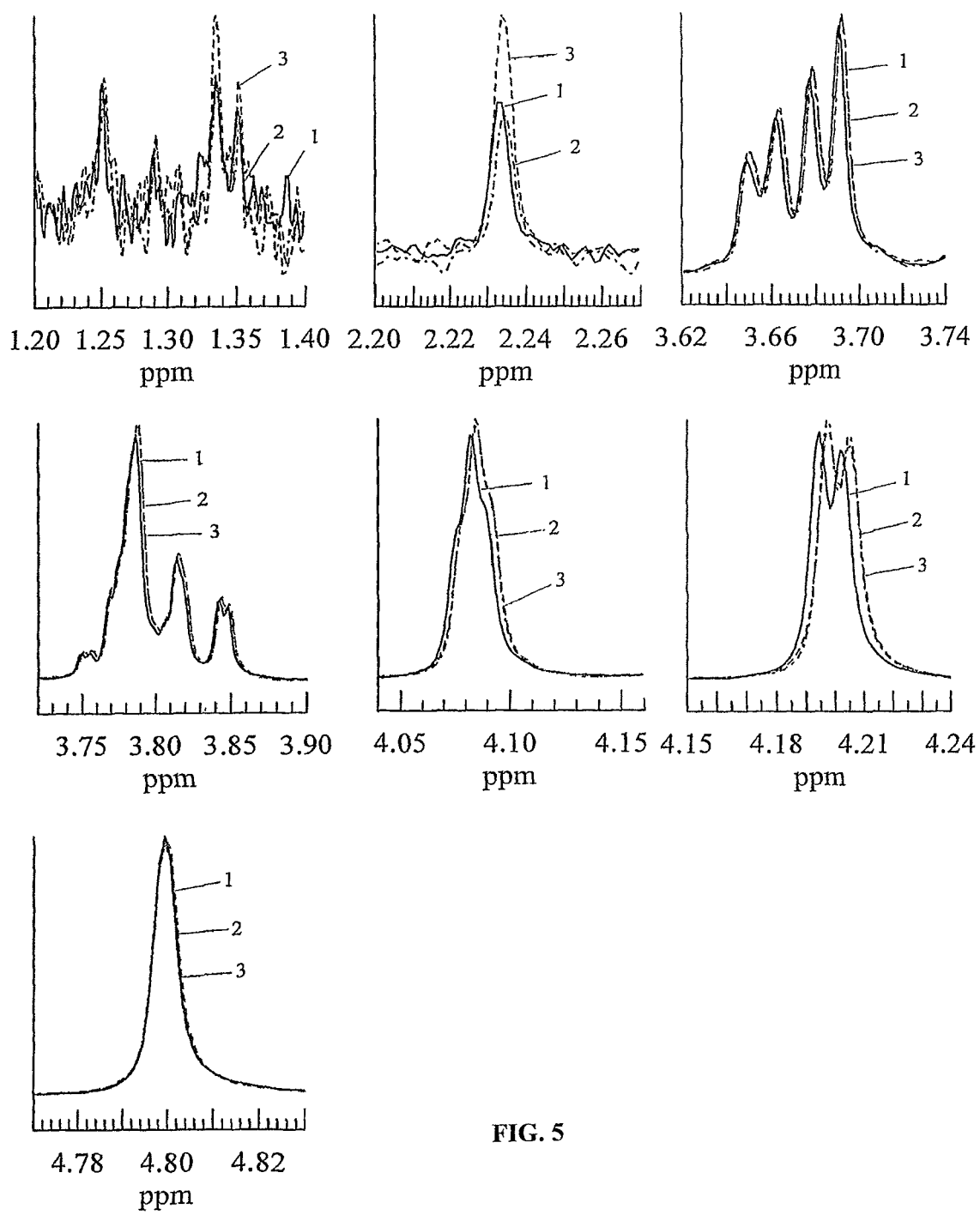

FIG. 4 and FIG. 5: NMR spectra on $^{13}$C and $^{1}$H nuclei, respectively, for the following samples:
aqueous solution of an initial crystalline gluconic acid calcium salt, curve 1;
aqueous solution of a mechanically activated amorphocrystalline gluconic acid calcium salt, curve 2;
aqueous solution of a mechanically activated amorphous gluconic acid calcium salt, curve 3.

NMR spectra were plotted on a pulse NMR spectrometer with Fourier transformation AVANCE-400 Bruker at the temperature of 295 K.

$^{13}$C NMR spectra of aqueous solutions of an amorphous form (FIG. 4, curves 3) and an amorphocrystalline composition (FIG. 4, curves 2) have a resonant absorption lines structure in the region of 62,8-179.2 ppm (FIG. 4, lines I) that is identical with the spectra of aqueous solutions of a crystalline gluconic acid calcium salt. The spectra of the amorphous form and amorphocrystalline composition differ only in that they have a chemical shift thru the value not exceeding 0.1 ppm with respect to the lines of the $^{13}$C NMR spectra of the aqueous solutions of a crystalline calcium gluconate.

In the $^{1}$H NMR spectra of aqueous solutions of an amorphous form (FIG. 5, curves 3) and an amorphocrystalline composition (FIG. 5, curves 2) there is observed a structure of the resonant lines of the $^{1}$H NMR spectra (FIG. 5, curves 1) in the area of 1.2-4.95 ppm that is similar to the spectra of aqueous solutions of a crystalline gluconic acid calcium salt. The spectra of the amorphous form and the amorphocrystalline composition differ only in that they have a chemical shift thru the value not exceeding 0.02 ppm with respect to the lines of the $^{1}$H NMR spectra of aqueous solutions of a crystalline calcium gluconate.

As can really be seen from data cited, at the time of machining a crystalline calcium gluconate in energy-strength grinding activator devices there takes place a change in its local molecular structure that brings about a shift of NMR absorption lines. It will be recalled that the value and direction of displacement are different for different lines. This behaviour might be elicited by several factors, specifically destruction of molecules, paramagnetism which is due to the formation of stable free radicals as well as a change in the conformation of the initial molecule upon completion of mechanical activation.

Figure 6:
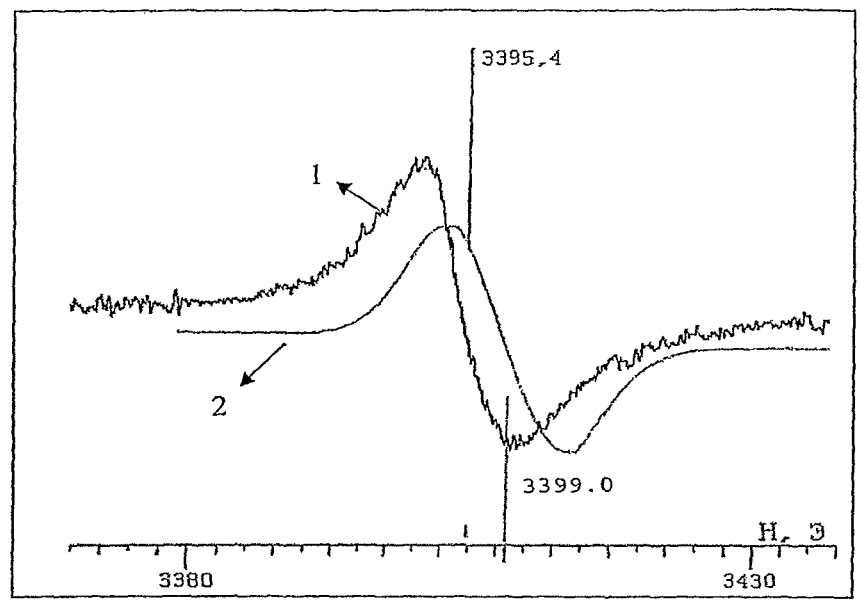

FIG. 6. EPR spectra of mechanically activated amorphous gluconic acid calcium salt (curve 1) and carbon standard (curve 2).

Figure 7:
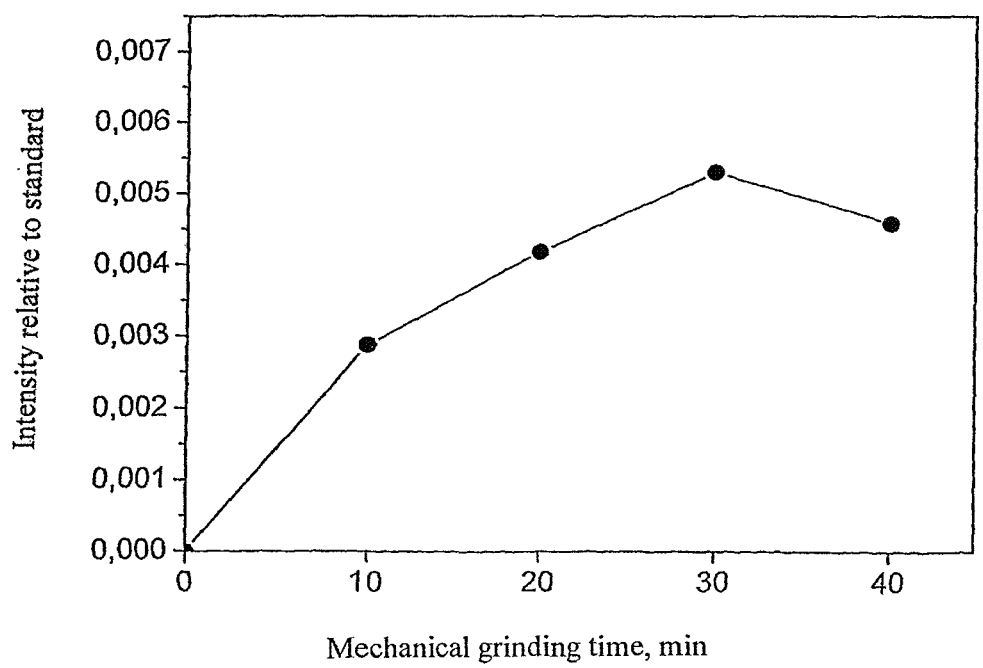

FIG. 7. EPR signal strength—gluconic acid calcium salt machining time curve.

EPR spectra were plotted on an EPR spectrometer VARIAN E-12 at a frequency of ~9.5 HHertz at 295 K. Normalization of intensity and determination of EPR lines g-factor were carried out in terms of a carbon standard (g=2.0030).

The EPR-spectrum of a mechanically activated amorphous calcium gluconate (FIG. 6, curve I) has an intensive EPR line with g≈2.005. In the initial sample of a crystalline gluconic acid calcium salt, an EPR signal is absent. EPR signal strength is increased as the content of an amorphous phase (calcium gluconate machining time) in an amorphocrystalline composition grows to reach the maximum value on achievement of an amorphous state. The EPR signal strength is preserved for a period of no less than 6 months, more exactly, the gluconic acid calcium salt machining brings about the formation of stable paramagnetic centers both in the amorphous phase and the intermediate amorphocrystalline composition.

From data cited there follows that the changes of a local atomic structure in machining in energy-strength grinding activator devices, of a crystalline gluconic acid calcium salt compound lead to the formation of chemically active stable paramagnetic centers, a factor that is likely to cause a change of both reactivity and biological activity of a substance to be obtained.

Figure 8:
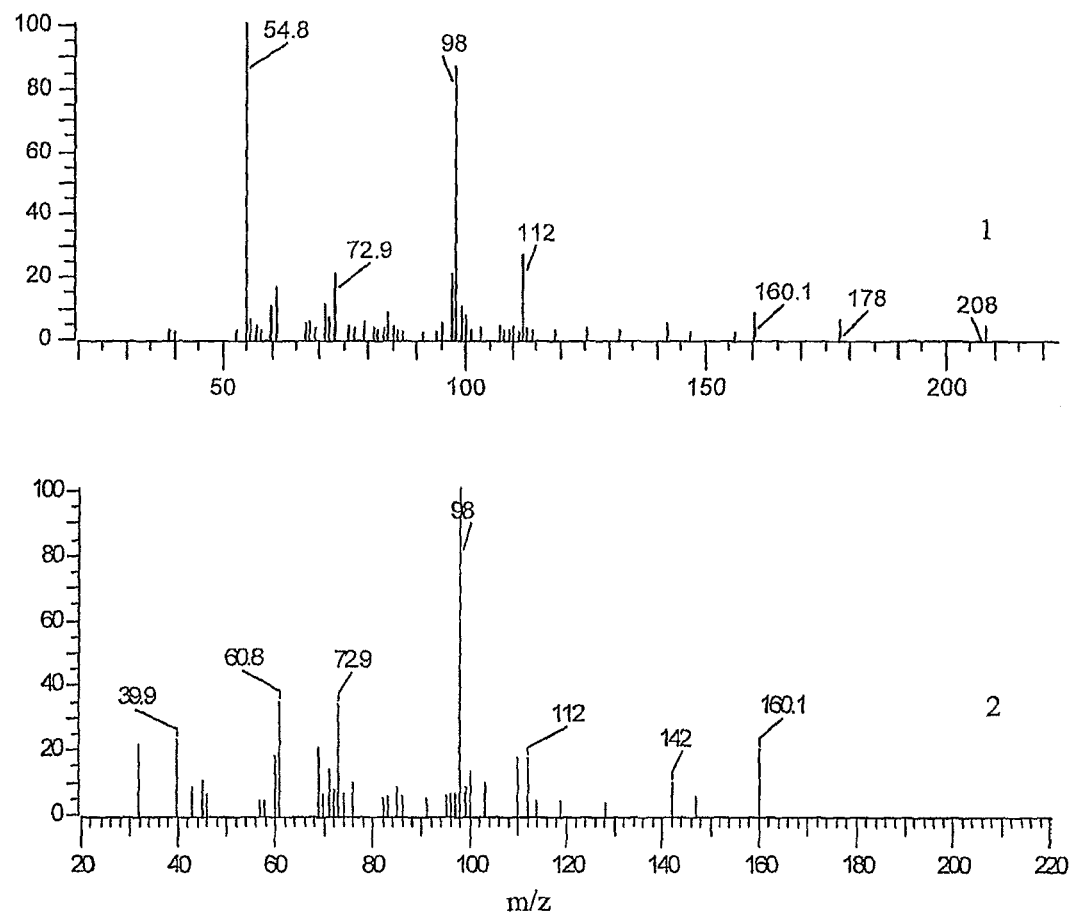

FIG. 8. Mass-spectra of electronic ionization (EI) of the following samples:
initial crystalline gluconic acid calcium salt, curve 1;
mechanically activated amorphous gluconic acid calcium salt, curve 2.

Mass-spectrometric measurements by a method of EI mass—spectrometry were made on a device MAT-212.

EI mass-spectra of mechanically activated samples in an amorphous and amorphocrystalline state do not differ from an initial crystalline gluconic acid calcium salt in principle. Likewise, while machining a calcium gluconate, no formation of new highly volatile compounds was discovered. The main distinction was revealed only in that in the EI mass-spectra of the mechanically activated amorphous form and amorphocrystalline composition there is observed a more intensive 160 m/z peak (FIG. 8, curve 2).

Figure 9:
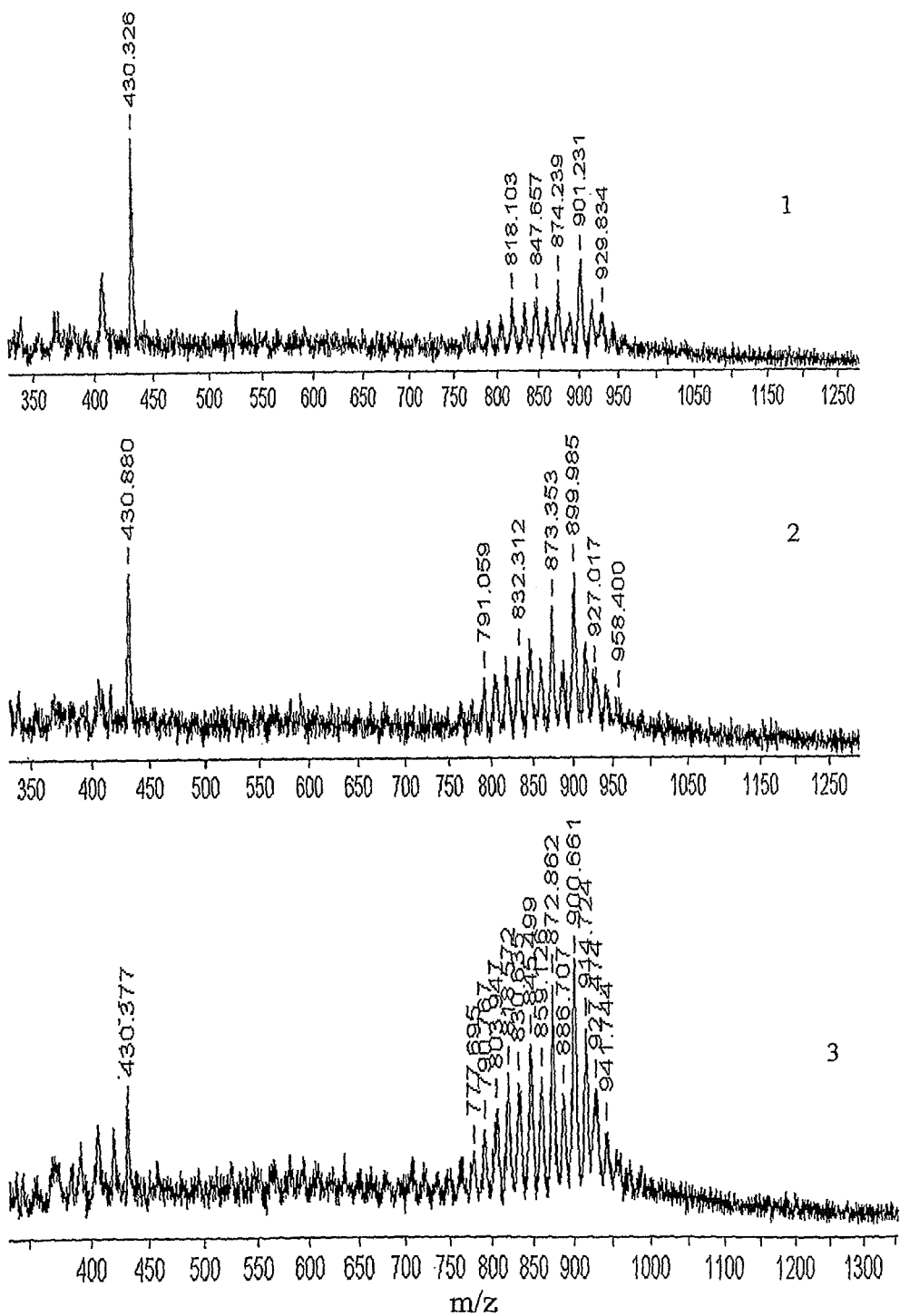

FIG. 9. Laser desorption mass-spectra from matrix (MALDI-TOF) of solutions of extracts in ethanol of the following samples:
  initial crystalline gluconic acid calcium salt, curve 1;
  mechanically activated amorphocrystalline gluconic acid calcium salt, curve 2;
  mechanically activated amorphous gluconic acid calcium salt, curve 3.

Mass-spectrometric measurements by a method of laser desorption mass-spectrometry from a matrix (MALDI-TOF) were made on a "DYNAMO" device. Research was carried out into the extracts of mechanically activated samples in water, ethanol, chloroform, and hexane.

FIG. 9: in the mass-spectrum of an extract of initial crystalline calcium gluconate (curve 1) there are high-molecular peaks of relatively low intensity in a m/z 750-950 region. In the mass-spectrum of the extract of the mechanically activated amorphocrystalline composition of an amorphous and crystal calcium gluconate (curve 2) the relative intensity of these peaks is increased appreciably. Even higher intensity of the high-molecular peaks in the m/z 750-950 region is observed in the mass-spectrum of the extract of a mechanically activated amorphous calcium gluconate (curve 3).

In the MALDI-TOF mass-spectra extracts of sample solutions in water and chloroform no appreciable differences were observed.

In general EI mass-stectrometric and MALDI-TOF data show that in machining a calcium gluconate, an amorphous composite or an amorphocrystalline composite and extracts thereof consist of a gluconic acid calcium salt of m/z=430 and the high-molecular compounds of a gluconic acid calcium salt having m/z from 470 to 950.

Figure 10:
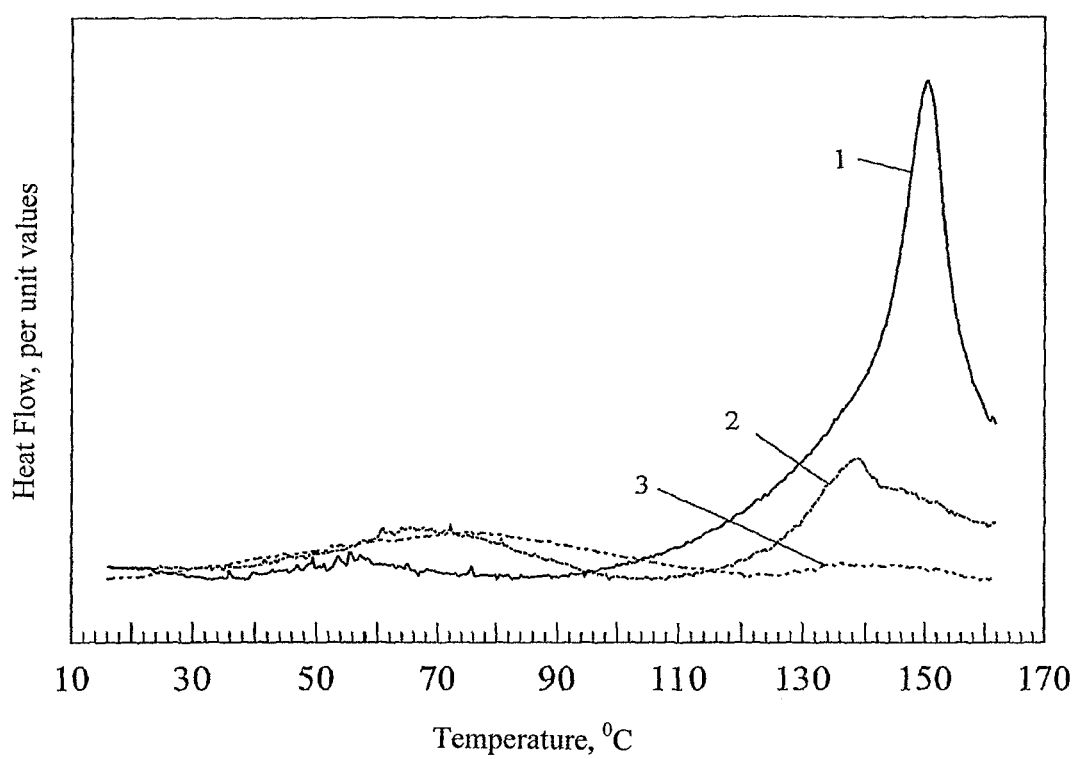

FIG. 10. Differential thermal analysis (DTA) curves of the following samples:
  initial crystalline gluconic acid calcium salt, curve 1;
  mechanically activated amorphocrystalline gluconic acid calcium salt, curve 2;
  mechanically activated amorphous gluconic acid calcium salt, curve 3.

DTA curves were plotted on a Shimazu DSC-60 device in an argon atmosphere at the rate of heating of 10° C./min. On an amorphous form DTA curve, endothermic peaks are substantially leveled in the range of temperatures of 125-165° C. and there is an additional endothermic peak in the range of temperatures of 30-100° C. (FIG. 10, curve 3). On an amorphocrystalline form DTA curve, the endothermic peak is increased in the range of temperatures of 30-100° C. and the endothermic peak is decreased in the range of temperatures of 125 to 165° C.

EXAMPLES OF REALIZATION OF METHODS

Example I

A Method for Producing a Mechanically Activated Amorphous Gluconic Acid Calcium Salt was Realized in the Following Manner.

A crystalline gluconic acid calcium salt in a weight ratio to grinding balls of 1:11 was loaded into. hermetic vessels and treated under inert atmosphere conditions in an energy-strength grinding activator device with an energy strength of 6 w/g (6 J/s.g) at a temperature not exceeding 60° C. for 30 min. The input specific energy value was equal to 10.8 kJ/g.

Considering the fact that rendering amorphous a crystalline calcium gluconate in an activator calls for no less than 10.5 kJ/g input specific energy, the treatable time was sufficient for providing an amorphous state. It is worthy of note that the treatable time depends on the energy strength of the activator. And with the energy strength of the activator of 3 W/g, the production of a mechanically activated amorphous gluconic acid calcium salt from a crystalline salt calls for I hour treatment and 30 minutes with the energy strength of 6 W/g.

Likewise, grinding was carried out under open atmosphere conditions, a residual atmosphere in an isolated volume, with gaseous media added to the open or isolated volume of a grinding device under vacuum conditions up to $10^4$ Pa.

Example 2

Method for Producing a Mechanically Activated Amorphocrystalline Gluconic Acid Calcium Salt A crystalline gluconic acid calcium salt in a weight ratio to grinding balls of 1:11 was loaded into hermetic vessels to be further treated under inert atmosphere conditions in an energy-strength grinding activator device with an energy strength of 6 W/g at a temperature not exceeding 60° C. for 10 minutes. The input specific energy value was equal to 3.6 kJ/g, which is not enough for completely rendering amorphous the initial crystalline state of an agent because the input specific energy value is no more than 10.4 kJ/g and, accordingly, a two-phase amorphocrystalline state was realized in the mechanically activated agent. And a mechanically activated product contained 90 wt. % of an amorphous phase and 10 wt. % of an crystal phase.

Grinding was also carried out under open atmosphere conditions, a residual atmosphere in an isolated volume, with a gaseous medium added to the open or isolated volume of a grinding device under vacuum conditions up to $10^{-4}$ Pa.

Example 3

Method for Producing a Mechanically Activated Amorphous Gluconic Acid Calcium Salt Compound with Pharmaceutically Acceptable Excipients A crystalline gluconic acid calcium salt in a weight ratio with pharmaceutically acceptable excipients (talc, starch, calcium stearate) of 94:2:2:2 was loaded into hermetic vessels in a weight ratio of a mixture to grinding balls of 1:11 to be treated under inert atmosphere conditions in an energy-strength grinding activator device with an energy strength of 6 W/g at a temperature not exceeding 60° C. for 30 minutes. The input specific energy value was 10.8 kJ/g, which is exceeds 10.5 kJ/g and is sufficient for forming an amorphous state.

Likewise, grinding was carried out under open atmosphere conditions, a residual atmosphere in an isolated volume, with a gaseous medium added to the open or isolated volume of a grinding device under vacuum conditions up to $10^{-4}$ Pa.

Example 4

Method for Producing a Mechanically Activated Amorphocrystalline Gluconic Acid Calcium Salt Composition with Pharmaceutically Acceptable Excipients A crystalline gluconic acid calcium salt in a weight ratio with pharmaceutically acceptable excipients (talc, starch, calcium stearate) of 94:2:2:2 was loaded into hermetic vessels in a weight ratio of a mixture to grinding balls of 1:11 to be treated under inert atmosphere conditions in an energy-strength grinding activator device with an energy strength of 6 W/g at a temperature of no more than 60° C. for 10 minutes. The input energy value was 3.6 kJ/g, which is not sufficient for completely rendering amorphous the initial crystalline state of an agent because the input specific energy was not greater than 10.4 kJ/g and, accordingly, a two-phase amorphocrystalline state was realized in a mechanically activated agent. And a mechanically activated product contained 90 wt. % of an amorphous phase and 10 wt. % of a crystal phase.

Likewise, grinding was carried out under open atmosphere conditions, a residual atmosphere in an isolated volume, with a gaseous medium added into the open or isolated volume of a grinding device under vacuum conditions up to $10^{-4}$ Pa.

Example 5

Mechanically activated amorphous compounds and composition obtainable in a therapeutically effective amount according to any one of the examples, were used as the active principle of pharmaceutical preparations. The preparations were used for administration using various methods, including peroral, transdermal ones, to mention only few. A suitable pharmaceutical form were powder, tablet, capsule, solution, gel, etc. A suitable amount of medicaments depended on age and general conditions in humans—from 200 mg to 6 g daily.

Mechanically activated amorphous compounds and compositions thus obtained were used perorally in doses of 1.5-3 g daily, a course of 15-30 days over a period of about 2 months in the group of 127 patients. Positive dynamics was observed in all the patients: reduced gum hemophilia and tooth neck sensitivity, disappearance of bad smell from the mouth, reduced tooth mobility and parodontal pocket, restoration of the physiological coloration of a gum mucous membrane. X-ray methods have revealed stabilization of maxilla and mandible bone structure and restoration of an osseous beams, restoration of osseous tissue structure with apical periodontitis. A course of treatment of patients with parodontal and tooth diseases reduced from 2.5-3 to 1.5-2 months. Calcium medicinals known in world medicine exhibit relatively much lower therapeutic efficacy or have it not at all in the treatment of such diseases.

The mechanically activated amorphous or amorphocrystalline state of a usable agent provides its unique preventive and therapeutic efficiency having no world analogs among other calcium-containing agents.

The preferable methods for executing the present invention are thus described in full. However, the afore-cited examples are merely an illustration of the invention and cannot be regarded as restricting the invention as to substance or scope.

Written source materials taken into account:

1. Ming S. Tang. Amorphous calcium compounds, a method for producing same, a method of treatment and remineralization of teeth, a compressed carbon-dioxide-saturated, amorphous calcium-compound-containing solution, a nonaqueous dispersion of carbonate and acid or its acid salt, a method for treating tooth tissue with the nonaqueous dispersion (U.S. Pat. No. 9,422,264, Published 27 May 1996).

2. Konygin G. N., Strelkov N. S. et al. Method of treatment of hypocalcemia, osteoporosis, fractures. Patent RF No 2268053. Published 20 Jan. 2006 (prototype).

The invention claimed is:

1. A mechanically activated amorphous gluconic acid calcium salt composition with the following ratio of ingredients, wt. %:

| | |
|---|---|
| gluconic acid calcium salt | 94-97 |
| talc | 2-1 |
| starch | 2-1 |
| calcium stearate | 2-1 | for treatment of dental or osseous diseases related to disorders of calcium metabolism in an organism, with a homogeneous diffuse halo in its powder X-ray diffraction diagram, expressed characteristically by shifting the centre of gravity of an absorption band of 3000-3600 $cm^{-1}$ to an area of great wave numbers thru the value of no more than 200 $cm^{-1}$, presence of an absorption band with frequencies 3308 ±20, 2933±10, 1602±10, 1420±10, with an arm of 1260±40, 1085±10, 1044±10, 877±10, 682±10, 577±10 $cm^{-1}$ and an additional absorption band having the frequency of 947±10 $cm^{-1}$ in an IR spectrum, reducing endothermal peaks in the temperature range of 125-165° C. and increasing a peak in the temperature range of 30-100° C. with a differential thermal analysis, presence of a single intensive line with a g-factor of 2.000 to 2.006 and a width of 8 to 9 E in an electronic paramagnetic resonance spectrum, occurrence of a fine structure unresolved wide line in the regions of 60-90 ppm and 170-190 ppm in $^{13}C$ NMR spectra, shifting the resonant lines of their aqueous solutions in an area of 62.8-179.2 ppm thru the value of no more than 0.1 ppm in $^{13}C$ NMR spectra, shifting the resonant lines of their aqueous solutions in an area of 1.2-4.95 ppm thru the value of no more than 0.02 ppm in $^{1}H$ NMR spectra, increasing intensities of 160 m/z peaks of mass-spectra not less than 2.5 times and 780-1000 m/z peaks of solution extracts thereof in ethanol not less than 3 times in a mass-spectroscopic analysis.

2. A mechanically activated amorphous gluconic acid calcium salt with a homogeneous diffuse halo in its powder X-ray diffraction diagram, expressed characteristically by a shift of the centre of gravity of an absorption band of 3000-3600 $cm^{-1}$ to a region of great wave numbers through the value of no more than 200 $cm^{1}$, presence of absorption bands with frequencies 3308±20, 2933±10, 1602±10, 1420±10, with an arm of 1260±40, 1085±10, 1044±10, 877±10, 682±10, 577±10 $cm^{-1}$ and an additional absorption band having a frequency of 947±10 $cm^{-1}$ in an IR spectrum, reducing endotherm peaks in the temperature range of 125-165° C. and increasing a peak in the temperature range of 30-100° C. with a differential thermal analysis, presence of a single intensive line with a g-factor from 2.000 to 2.006 and a width of 8 to 9 E in an electronic paramagnetic resonance spectrum, occurrence of a fine structure unresolved wide line in the regions of 60-90 ppm and 170-190 ppm in $^{13}C$ NMR spectra, and shifting the resonant lines of their aqueous solutions in the area of 62.8-179.2 ppm through the value of no more than 0.1 ppm in $^{13}C$ NMR spectra, shifting the resonant lines of their aqueous solutions in an area of 1.2-4.95 ppm through the value of no more than 0.02 ppm in $^{1}H$ NMR spectra, increasing intensities of 160 m/z peaks of mass-spectra not less than 2.5 times and 780-1000 m/z peaks of solution extracts thereof in ethanol not less than 3 times in a mass-spectroscopic analysis.

3. The pharmaceutical preparation for treatment of dental or osseous diseases related to disorders of calcium metabolism in an organism, in powder, tablet or powder capsule form, comprising a therapeutically effective amount of salt according to claim 2, and, if necessary, in mixture with pharmaceutically acceptable excipients.

4. A method of treatment of dental or osseous diseases related to disorders of calcium metabolism in an organism perorally, characterized in that use is made of a pharmaceutical preparation according to claim 3, in a dose of 0.2-6 g, 1-6 times daily, a course of no less than 1 month.

5. A mechanically activated amorphous gluconic acid calcium salt according to claim 2 which is produced by treating crystalline gluconic acid calcium salt in a grinding activator device for a suitable time for input specific energy of no less than 10.5 kJ/g.

6. A composition of amorphous gluconic acid calcium salt with pharmaceutically acceptable excipients for treatment of dental or osseous diseases related to disorders of calcium metabolism in an organism, characterized in that the salt of claim 2 and the exipients are mixed in the following ratio of ingredients, wt. %:

| | |
|---|---|
| mechanically activated amorphous gluconic acid calcium salt | 94-97 |
| talc | 2-1 |
| starch | 2-1 |
| calcium stearate | 2-1. |

7. A pharmaceutical preparation for treating dental or osseous diseases related to disorders of calcium metabolism in an organism in powder, tablet or powder capsule form, comprising a therapeutically effective amount of composition according to claim 6.

8. A method of treatment of dental or osseous diseases related to disorders of calcium metabolism in an organism perorally, characterized in that use is made of a pharmaceutical preparation according to claim 7, in a dose of 0.2-6 g, 1-6 times daily, a course of no less than 1 month.

\* \* \* \* \*

UNITED STATES PATENT AND TRADEMARK OFFICE
CERTIFICATE OF CORRECTION

| | |
|---|---|
| PATENT NO. | : 8,877,810 B2 |
| APPLICATION NO. | : 12/669907 |
| DATED | : November 4, 2014 |
| INVENTOR(S) | : Grigoriy Nikolaevich Konygin et al. |

It is certified that error appears in the above-identified patent and that said Letters Patent is hereby corrected as shown below:

Title page, Item (30) Foreign Application Priority Data: Please insert
--RUSSIA 2007127937 07/20/2007--.

Signed and Sealed this
Sixth Day of October, 2015

Michelle K. Lee
*Director of the United States Patent and Trademark Office*